United States Patent [19]

Manada et al.

[11] Patent Number: 5,426,209

[45] Date of Patent: Jun. 20, 1995

[54] PROCESS FOR PRODUCING A CARBONIC ACID DIESTER

[75] Inventors: Noriaki Manada; Toshio Kurafuji; Yasushi Yamamoto; Masato Murakami, all of Ube, Japan

[73] Assignee: Ube Industries, Ltd., Yamaguchi, Japan

[21] Appl. No.: 256,286

[22] PCT Filed: Nov. 5, 1993

[86] PCT No.: PCT/JP93/01610

§ 371 Date: Jul. 6, 1994

§ 102(e) Date: Jul. 6, 1994

[87] PCT Pub. No.: WO94/11335

PCT Pub. Date: May 26, 1994

[30] Foreign Application Priority Data

Nov. 6, 1992 [JP] Japan ............ 4-296971
Feb. 9, 1993 [JP] Japan ............ 5-21371

[51] Int. Cl.⁶ .................................. C07C 68/00
[52] U.S. Cl. ........................................ 558/277
[58] Field of Search ............................ 558/277

[56] References Cited

U.S. PATENT DOCUMENTS 4,318,862  3/1982  Romano et al. ............ 558/277
5,089,650  2/1992  Yokota et al. .............. 558/277
5,162,563  11/1992 Nishihira et al. ............ 558/260

FOREIGN PATENT DOCUMENTS 0503091   9/1992  European Pat. Off. .
60-75447  4/1985  Japan .
60-181051 9/1985  Japan .
63-72650  4/1988  Japan .
63-38018  7/1988  Japan .
3141248   6/1991  Japan .
4-89458   3/1992  Japan .
4139152   5/1992  Japan .
4139153   5/1992  Japan .
4297444   10/1992 Japan .

*Primary Examiner*—Mary C. Lee
*Assistant Examiner*—Michael G. Ambrose
*Attorney, Agent, or Firm*—Burgess, Ryand and Wayne

[57] ABSTRACT

The process of the present invention is characterized in that when a carbonic acid diester is produced by catalytically reacting carbon monoxide with a nitrous acid ester in the presence of a solid catalyst, a small amount of a chloroformic acid ester is mixed into a material gas containing the carbon monoxide and the nitrous acid ester and thereby the catalyst employed can be maintained at a high activity condition over a long time period, and the carbonic acid diester can be produced stably over a long time period at a high reaction rate and with a high selectivity.

18 Claims, No Drawings

PROCESS FOR PRODUCING A CARBONIC ACID DIESTER

This application is a continuation pursuant to 35 U.S.C. §371 of International Application No. PCT/JP93/01610, filed Nov. 5, 1993.

TECHNICAL FIELD

The present invention relates to a process for producing a carbonic acid diester, for example, a carbonic acid dialkylester, from carbon monoxide and a nitrous acid ester. Particularly, the present invention relates to a process for selectively producing a carbonic acid diester at a high stability over a long time at a high reaction rate by mixing a chloroformic acid ester into a starting material gas containing carbon monoxide and nitrous acid ester, and subjecting the mixed material gas to a catalytic reaction in the presence of a solid catalyst.

The carbonic acid diesters are industrially very useful as intermediates of polymers such as polycarbonates and polyurethane, as synthesis materials of various chemical reagents, and as solvents.

BACKGROUND ART

A conventional method of producing a carbonic acid diester by a reaction of phosgene with an alcohol is a well known and very old method that has been practiced for some time. Nevertheless, this conventional method is disadvantageous in that phosgene has an extremely strong toxicity, and thus is not preferable as a starting material in view of environmental and health considerations. Also, since the reaction of the conventional method produces hydrochloric acid as a by-product, which corrodes the reaction device, an expensive material must be selected and employed for the reaction apparatus.

Therefore, there is a strong demand for a new method of producing a carbonic acid diester without using phosgene, in consideration of the environmental and health and industrial difficulty.

In response to this demand, various attempts have been made to produce a carbonic acid diester from an alcohol and carbon monoxide, as disclosed in, for example, Japanese Unexamined Patent Publication (Kokai) No. 60-75,447, and 63-72,650, and Japanese Examined Patent Publication (Kokoku) 63-38,018.

In those methods, the carbonic acid diester is produced by a catalytic oxygen-oxidizing reaction of carbon monoxide with an alcohol in a liquid phase, in the presence of a catalyst consisting of a copper halide or palladium halide. These methods are disadvantageous in that, in the catalytic oxygen-oxidizing reaction, carbon dioxide is produced as a by-product, and thus the production of the carbonic acid diester is effected with a low selectivity based on the amount of carbon monoxide supplied to the reaction system, and the catalytic oxygen-oxidizing reaction produces water as another by-product, and thus the isolation of the resultant carbonic acid diester is difficult. Further, the methods as disclosed in the above-mentioned publications are not always industrially advantageous in that the reactions of the conventional methods are liquid phase reactions and thus a procedure for separating the resultant product from the catalyst is necessary.

There have been attempts made to eliminate the above-mentioned disadvantages, and as one such attempt, Japanese Unexamined Patent Publication (Kokai) No. 60-181,051 discloses a method of producing carbonic acid diester by a catalytic oxidizing reaction of a nitrous acid ester with carbon monoxide, in a gas phase, in the presence of a catalyst composed of a solid platinum group metal or compound thereof carried on a solid carrier and an oxidant in an amount of 10 molar % in terms of $O_2$, per mole of carbon monoxide present in the reaction mixture.

This method however, is disadvantageous in that the oxidant in the above-mentioned specific amount based on the carbon monoxide effectively inhibits a production of oxalic acid diester as a by-product, but the addition of the oxidant in the above-mentioned specific amount based on the carbon monoxide cannot completely inhibit the production of the oxalic acid diester, and therefore, the target carbonic acid diester is produced with an unsatisfactorily low selectivity, and the reaction rate and the durability of the catalyst are unsatisfactory.

Further, the above-mentioned method is further disadvantageous in that the proportion of nitrous acid ester in a reaction mixed gas comprising the nitrous acid ester, carbon monoxide, alcohol and oxygen is higher than an explosion (flammable) limit of the mixed gas, and thus this reaction mixed gas is not industrially satisfactory in view of the safety of the procedure.

Japanese Unexamined Patent Publication (Kokai) Nos. 3-141,243 and 4-139,152 disclose a method of producing dimethyl carbonate by a catalytic reaction of carbon monoxide with methyl nitrite in a gas phase by using a catalyst comprising a carrier, for example, activated carbon, and a catalytic member selected from compounds of platinum group metals, for example, palladium chloride and palladium sulfate, and compounds of metals selected from iron, copper, bismuth, cobalt, nickel and tin, and carried on the carrier. This method is unsatisfactory in catalytic activity and durability of the catalyst for practical use in industry.

As mentioned above, the conventional methods of producing carbonic acid diester by using a nitrous acid ester are unsatisfactory in the durability of the catalyst and are not always satisfactory in reaction rate and selectivity of the carbonic acid diester.

DISCLOSURE OF THE INVENTION

An object of the present invention is to provide an industrially appropriate process for producing a carbonic acid diester, by which process the carbonic acid diester can be stably produced while maintaining the reaction rate and selectivity of the carbonic acid diester at high levels over a long time period, with substantially no catalyst deterioration. Particularly, in a practical fixed bed type gas phase process, it is important that a catalyst holds its catalytic activity at a high level over a long time, and thus the present invention intends to provide a process for producing the carbonic acid diester which can satisfy the above-mentioned requirements.

The inventors of the present invention have energetically studied a process for synthesizing a carbonic acid diester by a catalytic reaction of carbon monoxide with a nitrous acid ester to solve the above-mentioned problems on the conventional processes for producing the carbonic acid diester. As a result, it was found that the carbonic acid diester can be produced as a target product at a high reaction rate with a high selectivity by using a solid catalyst and mixing a chloroformic acid ester into a material gas containing carbon monoxide and nitrous acid ester, while maintaining a catalytic activity at a high level over a long time, and thus the present invention was completed.

The process of the present invention for producing a carbonic acid diester comprises catalytically reacting carbon monoxide with a nitrous acid ester in the presence of a solid catalyst in which a platinum group metal or a compound thereof is carried on a carrier, to produce a carbonic acid diester, and is characterized in that a chloroformic acid ester is mixed into a material gas containing the carbon monoxide and the nitrous acid ester, and the mixed material gas is brought into contact with the solid catalyst.

BEST MODE OF CARRYING OUT THE INVENTION

The process of the present invention will be explained in detail hereinafter.

The nitrous acid ester usable for the process of the present invention is preferably selected from nitrous acid esters of lower aliphatic monohydric alcohols having 1 to 4 carbon atoms, for example, methyl nitrite, ethyl nitrite, n- (or iso-) propyl nitrite, n- (or iso-) butyl nitrite and sec-butyl nitrite; nitrous acid esters of cycloaliphatic alcohols, for example, cyclohexyl nitrite; and nitrous acid esters of aralkyl alcohols, for example, phenylethyl nitrite. Among those esters, more preferably the nitrous acid esters of lower aliphatic monohydric alcohols having 1 to 4 carbon atoms are employed and most preferably methyl nitrite and ethyl nitrite are employed.

As a preferably chloroformic acid ester usable for the present invention, chloroformic acid esters of lower aliphatic monohydric alcohols having 1 to 4 carbon atoms, for example, methyl chloroformate, ethyl chloroformate, n- (or iso-) propyl chloroformate, n- (or iso-) butyl chloroformate, and sec-butyl chloroformate; chloroformic acid esters of cycloaliphatic alcohols, for example, cyclohexyl chloroformate; and chloroformic acid esters of aralkyl alcohols, for example, phenylethyl chloroformate are pointed out. Usually, a chloroformic acid ester having the same ester-forming group, for example, alkyl group, cycloaliphatic alkyl group or aralkyl group, as that of the nitrous acid ester employed, is used. It should be noted that the carbonic acid diester obtained by the process of the present invention is a compound having the same ester-forming group, for example, alkyl, cycloaliphatic or aralkyl group, as that of the nitrous acid ester and the chloroformic acid ester used.

In the process of the present invention, there is no specific limitation to the amount of the chloroformic acid ester mixed in the material gas containing the carbon monoxide and nitrous acid ester. However, if the amount of the chloroformic acid ester is too large, it causes an economical disadvantage. Therefore, the amount of the chloroformic acid ester to be contained in the mixed material gas is preferably 1% or less, more preferably 0.01 to 1% by volume, based on the total volume of the mixed material gas. If the amount of the mixed chloroformic acid ester is too small, the effect derived from the mixed chloroformic acid ester becomes insufficient. The amount of the chloroformic acid ester to be mixed is preferably 1000 ppm or less, more preferably 50 to 1000 ppm, based on the total volume of the mixed material gas.

In the process of the present invention, the chloroformic acid ester mixed to the material gas effectively causes the catalytic activity of the solid catalyst to be maintained at a high level, the reaction of the nitrous acid ester with carbon monoxide to be carried out at a high reaction rate and the resultant carbonic acid diester to be produced at a high selectivity.

As a solid catalyst usable for the process of the present invention, a catalyst composed of a carrier consisting of activated carbon, alumina, diatomaceous earth, silicon carbide, or titania and a platinum group metal or platinum group metal compound carried on the carrier, or another catalyst composed of the carrier as mentioned above and the platinum group metal or platinum group metal compound and a compound of at least one other metal selected from the group consisting of iron, copper, bismuth, cobalt, nickel and tin, carried on the above-mentioned carrier, can be employed.

The platinum group metal usable for the solid catalyst for the process of the present invention is preferably selected from for example, palladium, ruthenium and rhodium, and the platinum group metal compound is preferably selected from, for example, halides of the platinum group metals, for example, palladium chloride, palladium bromide, palladium iodide, palladium fluoride, ruthenium chloride and rhodium chloride; and nitric acid salts, sulfuric acid salts and acetic acid salts of the platinum group metals, for example, palladium nitrate, palladium sulfate and palladium acetate, more preferably from palladium chloride, palladium bromide, palladium nitrate and palladium sulfate. Also, the compound of another metal preferably includes compounds of, for example, iron, copper, bismuth, cobalt, nickel and tin, more preferably halides, for example, chlorides, bromides, iodides and fluorides, inorganic acid salts, for example, nitrates, sulfates and phosphates, and organic acid salts, for example, acetates, of the above-mentioned metals, still more preferably, the halide and sulfates of the above-mentioned metals.

With respect to the solid catalyst usable for the process of the present invention, the amount of the platinum group metal or platinum group metal compound to be carried on the carrier is preferably 0.1 to 10% by weight, more preferably 0.5 to 2% by weight, in terms of the platinum group metal, based on the weight of the carrier. The amount of another metal compound, for example, the compound of iron, copper, bismuth, cobalt, nickel or tin is preferably 0.1 to 5 gram atom equivalent, more preferably 1 to 10 gram atom equivalent, in terms of the metal, based on the amount of the platinum group metal.

In the process of the present invention, the solid catalyst may be in the form of any of a powder, a grain or a shaped article, and the size of the catalyst is not limited to a specific range of the size. For example, the solid catalyst in the form of a powder usually has a size of from 20 to 100 $\mu$m, the other catalyst in the form of grains usually has a 4 to 200 mesh size, and the shaped catalyst preferably has a size of several mm.

In the process of the present invention, not only can a newly prepared fresh solid catalyst be employed, but also a catalyst which has been employed in a reaction of carbon monoxide with a nitrous acid ester for producing a carbonic acid diester, and thus has a reduced activity, can be reused. Also, the catalyst having a reduced activity is treated with hydrogen, and then the reactivated catalyst can be used for the process of the present invention.

In the above-mentioned treatment with hydrogen, an inert gas, for example a nitrogen or argon gas containing hydrogen can be used as a treating gas, and the treatment may be applied to the solid catalyst under appropriately selected conditions from space velocities of from 0 to 20,000 hr$^{-1}$, preferably 50 to 10,000 hr$^{-1}$, pressures of from 1 to 100 atmospheres, preferably 1 to 20 atmospheres, temperatures of from 70° to 500° C., preferably from 100° to 450° C. and treating times of from several hours to several tens of hours.

It is one of the advantages of the process of the present invention that the catalytic reaction of carbon monoxide with a nitrous acid ester can be carried out under very mild conditions. For example, in the process of the present invention, the catalytic reaction of carbon monoxide with the nitrous acid ester can be effected at a temperature controlled to a level of from 0° to 200° C., preferably from 50° to 140° C. under a pressure regulated to a level of from the ambient atmospheric pressure to 20 kg/cm$^2$G. Of course, in the process of the present invention the reaction can be carried out in a pressurized system, for example, under a pressure of from 1 to 20 kg/cm$^2$G and at a temperature in the range of from 50° C. to 140° C., without difficulty.

Also, in the process of the present invention, the contact of carbon monoxide with the nitrous acid ester can be effected in any style, for example, in a gas phase or liquid phase, or in a batch system or continuous system. In industrial view point, the reaction is advantageously carried out in a gas phase in a continuous system. In this catalytic reaction, the catalyst in the reaction system may be placed in a fixed bed or in a fluidized bed.

The nitrous acid ester usable as a starting material of the process of the present invention can be easily synthesized, for example, by decomposing an aqueous sodium nitrite solution with nitric acid or sulfuric acid and thereby generating a mixed gas consisting of nitrogen monoxide (NO) and nitrogen dioxide (NO$_2$), oxidizing a portion of the NO in the mixed gas with molecular oxygen to produce NO$_2$, preparing a NO$_x$ gas containing NO and NO$_2$ in a volume ratio of NO/NO$_2$ of 1/1, and bringing an alcohol compound into contact with the NO$_x$ gas. In consideration of the synthesis of nitrous acid ester in addition of the process of the present invention, the catalytic reaction of carbon monoxide with a nitrous acid ester in accordance with the process of the present invention is desirably carried out in a relatively low pressure system having a pressure of about 2 to 3 kg/cm$^2$G in industrial practice.

For additional information, the nitrous acid ester gas prepared by the above-mentioned synthesis contains non-reacted fractions of the alcohol compound and nitrogen oxides (particularly nitrogen monoxide) and optionally a small amount of water, in addition to the nitrous acid ester. Nevertheless, in the process of the present invention, even when the non-refined nitrous acid ester gas is employed as a source of nitrous acid ester, a good result can be obtained.

In the process of the present invention, it is preferable that the material gas comprising carbon monoxide and the nitrous acid ester are fed to the above-mentioned reactor after being diluted with an inert gas, for example, nitrogen gas. In this case, the composition of the material gas is not limited to a specific range thereof from the viewpoint of the reaction. However from the viewpoint of safety, the concentration of the nitrous acid ester in the material gas is preferably 20% by volume or less, more preferably 5 to 20% by volume.

With respect to the concentration of carbon monoxide in the mixed material gas usable for the process of the present invention, when the nitrous acid ester is fed in the state such that it is diluted by carbon monoxide in place of the inert gas, the concentration of carbon monoxide can be raised up to 80% by volume. However, in an industrial production process, it is preferable that a carbon monoxide gas and a nitrous acid ester gas are recycled and reused, and a portion of the recycled gas is discharged to the outside of the reaction system. Further, since the conversion of carbon monoxide per one cycle reaction is about 20 to 30%, an increase in the concentration of carbon monoxide to more than 20% by volume merely results in an increase in loss thereof, and a reduction in the concentration of carbon monoxide to a level of less than 5% by volume disadvantageously causes reduction in productivity. Accordingly, in practice, the concentration of carbon monoxide in the material gas is preferably controlled to a range of from 5 to 20% by volume from an economical viewpoint.

In the process of the present invention, the molar ratio of carbon monoxide to the nitrous acid ester in the material gas is preferably in a range of 0.1 to 10 moles, more preferably 0.25 to 2 moles, per mole of the nitrous acid ester. Also the mixed material containing carbon monoxide and the nitrous acid ester is fed into the reactor preferably at a space velocity (GHSV) of 500 to 50,000 hr$^{-1}$, more preferably 2,000 to 40,000 hr$^{-1}$.

In the process of the present invention, after the material gas containing carbon monoxide and a nitrous acid ester is fed into a reactor and before they are subjected to a catalytic reaction in the presence of a solid catalyst, a chloroformic ester is added, as a pre-treating step, to the material gas containing the carbon monoxide and nitrous acid ester. When a small amount of the chloroformic acid ester is added to the material gas, an inert gas such as a nitrogen gas flows on a warmed chloroformic acid ester layer so as to allow a vapor of the chloroformic acid ester to accompany the flow of the inert (nitrogen) gas and the resultant chloroformic acid ester-containing inert gas is mixed with the material gas; or a vaporizer for the chloroformic acid ester is connected, separately from a feed conduit for the material gas, to a reactor, a chloroformic acid ester gas generated in the vaporizer is caused to accompany an inert gas (nitrogen gas), and is then mixed with the material gas; or a liquid chloroformic acid ester is directly added dropwise to the material gas and the mixed gas flows through a warmed vaporizer to vaporize the chloroformic acid ester and thereby to allow the chloroformic acid ester vapor to uniformly diffuse into the material gas. From the above method of addition, an appropriate method usable for industrial practice can be selected and utilized so that the concentration of the chloroformic acid ester in the mixed material gas can thereby be controlled to a desired level and the carbonic acid diester can be selectively produced with a high stability over a long time at a high reaction rate.

The type of the carbonic acid ester produced by the production process of the present invention is variable depending on the type of the nitrous acid ester employed, and it may be carbonic acid dialkyl esters, for example, dimethyl carbonate, diethyl carbonate, and dipropyl carbonate; dicyclohexyl carbonate and dibenzyl carbonate. Particularly, by the process of the present invention, di-lower alkyl esters of carbonic acid, for example, dimethyl carbonate, can be produced at a high selectivity and at a high yield.

After the above-mentioned catalytic reaction is completed, a reaction mixture comprising the target carbonic acid diester, a by-product such as an oxalic acid diester, non-reacted carbon monoxide and nitrous acid diester, chloroformic acid ester, nitrogen monoxide, carbon dioxide, an inert gas and a small amount of water, is discharged from the reactor. From this reaction mixture, the carbonic acid diester can be easily refined and isolated by a known method, for example, distillation or the like, separately, by recycling a non-condensed gas containing the carbon monoxide, nitrous acid ester, chloroformic acid ester, nitrogen monoxide, carbon dioxide, inert gas and small amount of water through the reactor while discharging a portion of the gas, so the target carbonic acid diester can be continuously produced at a high stability over a long time period.

EXAMPLES

The present invention will be further explained by the following specific examples which are merely representative and do not restrict the scope of the present invention.

In the examples and comparative examples, the space time yield (STY) Y in g/l·hr of a carbonic acid diester was calculated from a catalytic reaction time $\theta$ in hours of carbon monoxide with a nitrous acid ester, an amount a in grams of the carbonic acid diester produced during the reaction time and an amount b in liters of a catalyst packed in a reaction tube in accordance with the following equation:

$$Y(in\ g/l\cdot hr) = a/(b \approx \theta)$$

Also, in each of the examples and comparative examples, the selectivity X in % of the carbonic acid diester was calculated from an amount c in moles of the carbonic acid diester, an amount d in moles of oxalic acid diester and an amount e in moles of carbon dioxide produced during the catalytic reaction time $\theta$, based on the amount of carbon monoxide fed into the reaction system, in accordance with the following equation.

$$X(in\%) = [c/(c + 2 \times d + e)] \times 100$$

Further, in each of the examples and comparative examples, the activity reduction D in %/hr of the catalyst was calculated from a space time yield $Y_o$ in g/l·hr of the carbonic acid diester at an initial stage of the reaction (at a stage of 2 hours after the start of the reaction) and a space time yield $Y_t$ in g/l·hr of the carbonic acid diester at a stage of a time t in hours after the start of the reaction, in accordance with the following equation:

$$D\ in\ \%/hr = [(Y_o - Y_t)/Y_o](t-2) \times 100$$

The solid catalysts used in the examples and comparative examples were prepared as follows.

CATALYST A

A Pd-Cu-containing solution was prepared by heat-dissolving 0.83g of palladium chloride ($PdCl_2$) and 1.60g of copper (II) chloride ($CuCl_2 \cdot 2H_2O$) in 70 ml of a 5% ammonia aqueous solution at a temperature of 70° C. to 80° C. To this solution, 50g of a fully dried activated carbon was mixed, the resultant mixture was stirred for one hour to impregnate the activated carbon with the Pd-Cu-containing solution. Thereafter, water was evaporated away from the mixture at a temperature of 80° C. under a reduced pressure, and the residual mixture was heat-treated at 200° C, for one hour in a nitrogen gas flow to prepare a solid catalyst. The amounts of the metal compounds in the resultant solid catalyst were measured. In the results of the measurement, the amount of the Pd compound contained in the catalyst was, in terms of Pd metal, 1% by weight, and the atomic ratio of Cu/Pd was 2.

CATALYST B

A Pd-Cu-containing solution was prepared by heat-dissolving 0.83g of palladium chloride ($PdCl_2$) and 1.60g of copper (II) chloride ($CuCl_2 \cdot 2H_2O$) in 70 ml of an 1N HCl aqueous solution at a temperature of 70° C. to 80° C. Into this solution, 50g of a fully dried activated carbon was mixed, the resultant mixture was stirred for one hour to impregnate the activated carbon with the Pd-Cu-containing solution. Thereafter, water was evaporated away from the mixture at a temperature of 80° C. under a reduced pressure, and the residual mixture was heat-treated at 200° C. for one hour in a nitrogen gas flow to prepare a solid catalyst. The amounts of the metal compounds in the resultant solid catalyst were measured. In the results of the measurement, the amount of the Pd compound contained in the catalyst was, in terms of Pd metal, 1% by weight, and the atomic ratio of Cu/Pd was 2.

CATALYST C

A Pd-containing solution was prepared by heat-dissolving 0.83g of palladium chloride ($PdCl_2$) in 70 ml of a 5% ammonia aqueous solution at a temperature of 70° C. to 80° C. To this solution, 50g of a fully dried activated carbon was mixed, the resultant mixture was stirred for one hour to impregnate the activated carbon with the Pd-containing solution. Thereafter, water was evaporated away from the mixture at a temperature of 80° C. under a reduced pressure, and the residual mixture was heat-treated at 200° C. for one hour in a nitrogen gas flow to prepare a solid catalyst. The amount of the metal compound in the resultant solid catalyst was measured. In the result of the measurement, the amount of the Pd compound contained in the catalyst was, in terms of Pd metal, 1% by weight.

CATALYST D

A Pd-containing solution was prepared by heat-dissolving 0.83g of palladium chloride ($PdCl_2$) in 70 ml of an 1N HCl aqueous solution at a temperature of 70° C. to 80° C. To this solution, 50g of a fully dried activated carbon was mixed, the resultant mixture was stirred for one hour to impregnate the activated carbon with the Pd-containing solution. Thereafter, water was evaporated away from the mixture at a temperature of 80° C. under a reduced pressure, and the residual mixture was heat-treated at 200° C. for one hour in a nitrogen gas flow to prepare a solid catalyst. The amount of the metal compound in the resultant solid catalyst was measured. In the result of the measurement, the amount of the Pd compound contained in the catalyst was, in terms of Pd metal, 1% by weight.

EXAMPLE 1

A gas phase reaction tube (equipped with an outside jacket) having an inside diameter of 13 mm, was packed with 1.0 ml of the solid catalyst A as mentioned above, and fixed vertically. Then, a heating medium was circulated through the outside jacket of the reaction tube to heat-control the temperature of the catalyst layer to 120° C.

A material gas containing a methyl nitrite-containing gas prepared from nitrogen monoxide, oxygen and methyl alcohol, and carbon monoxide was mixed with a methyl chloroformate-containing nitrogen gas prepared by passing the nitrogen gas through a methyl chloroformate bath. The resultant mixed material gas contained 7% by volume of methyl nitrite, 7% by volume of carbon monoxide, 3% by volume of nitrogen monoxide, 5% by volume of methyl alcohol, 500 ppm by volume of methyl chloroformate and 78% by volume of nitrogen. After passing through a 5° C. cold trap, the mixed material gas was fed into the reaction tube through a top portion thereof at a gas hourly space velocity (GHSV) of 30,000 hr$^{-1}$ to cause a reaction to be carried out under the ambient atmospheric pressure. Next, the resultant reaction product discharged from the reaction tube was collected in an ice-cooled methyl alcohol. The collected liquid was analysed by means of a gas-chromatography. As a result, at a stage of 2 hours after the start of the reaction, the STY of dimethyl carbonate was 437 g/l·hr and the selectivity of dimethyl carbonate was 92%. Also, at a stage of 8 hours after the start of the reaction, the STY of dimethyl carbonate was 464 g/l·hr and the selectivity of dimethyl carbonate was 93%. Due to the methyl chloroformate addition effect, no catalyst activity reduction was detected during the above-mentioned reaction time. Rather, it was found that the catalyst activity was enhanced by the addition of methyl chloroformate. Namely, the catalyst activity reduction D was −1.0%/hr.

COMPARATIVE EXAMPLE 1

Dimethyl carbonate was prepared by the same procedures as in Example 1 except that the mixed material gas contained no methyl chloroformate.

At a stage of 2 hours after the start of the reaction, the STY of dimethyl carbonate was 438 g/l·hr and the selectivity thereof was 92%. Also, at a stage of 8 hours after the start of the reaction, the STY of dimethyl carbonate was 223 g/l·hr and the selectivity thereof was 83%. From these results, the catalyst activity reduction D was 8.2%/hr and unsatisfactory.

EXAMPLE 2

Dimethyl carbonate was prepared by the same procedures as in Example 1 except that the concentration of methyl chloroformate in the mixed material gas was controlled to a level of 90 ppm by volume.

At a stage of 2 hours after the start of the reaction, the STY of dimethyl carbonate was 444 g/l·hr and the selectivity thereof was 94%. Also, at a stage of 8 hours after the start of the reaction, the STY of dimethyl carbonate was 432 g/l·hr and the selectivity thereof was 93%. From these results, the catalyst activity reduction D was 0.5%/hr.

EXAMPLE 3

Dimethyl carbonate was prepared by the same procedures as in Example 1 except that the concentration of methyl chloroformate in the mixed material gas was controlled to a level of 60 ppm by volume.

At a stage of 2 hours after the start of the reaction, the STY of dimethyl carbonate was 314 g/l·hr and the selectivity thereof was 94%. Also, at a stage of 8 hours after the start of the reaction, the STY of dimethyl carbonate was 292 g/l·hr and the selectivity thereof was 92%. From these results, the catalyst activity reduction D was 1.2%/hr.

EXAMPLE 4

Dimethyl carbonate was prepared by the same procedures as in Example 1 except that the concentration of methyl chloroformate in the mixed material gas was controlled to a level of 50 ppm by volume.

At a stage of 2 hours after the start of the reaction, the STY of dimethyl carbonate was 315 g/l·hr and the selectivity thereof was 94%. Also, at a stage of 8 hours after the start of the reaction, the STY of dimethyl carbonate was 270 g/l·hr and the selectivity thereof was 92%. From these results, the catalyst activity reduction D was 2.4%/hr.

EXAMPLE 5

Dimethyl carbonate was prepared by the same procedures as in Example 1 except that the concentrations of carbon monoxide and nitrogen in the mixed material gas were controlled to 16% by volume and 69% by volume, respectively.

At a stage of 2 hours after the start of the reaction, the STY of dimethyl carbonate was 483 g/l·hr and the selectivity thereof was 92%. Also, at a stage of 8 hours after the start of the reaction, the STY of dimethyl carbonate was 598 g/l·hr and the selectivity thereof was 92%. Due to the methyl chloroformate addition effect, no catalyst activity reduction was detected, and rather a catalyst activity-enhancing effect was recognized. From these results, the catalyst activity reduction D was −4.0%/hr.

EXAMPLE 6

Dimethyl carbonate was prepared by the same procedures as in Example 1 except that the catalyst A was employed in an amount of 3.0 ml and the mixed material gas was fed at a space velocity (GHSV) of 10,000 hr$^{-1}$.

At a stage of 2 hours after the start of the reaction, the STY of dimethyl carbonate was 402 g/l·hr and the selectivity thereof was 95%. Also, at a stage of 8 hours after the start of the reaction, the STY of dimethyl carbonate was 411 g/l·hr and the selectivity thereof was 94%. Due to the addition effect of methyl chloroformate, no activity reduction of the catalyst occurred. From these results, the catalyst activity reduction D was −0.37%/hr.

EXAMPLE 7

Dimethyl carbonate was prepared by the same procedures as in Example 1 except that the catalyst A was replaced by catalyst B.

At a stage of 2 hours after the start of the reaction, the STY of dimethyl carbonate was 520 g/l·hr and the selectivity thereof was 91%. Also, at a stage of 8 hours after the start of the reaction, the STY of dimethyl carbonate was 502 g/l·hr and the selectivity thereof was 90%. From these results, the catalyst activity reduction D was 0.59%/hr.

EXAMPLE 8

Dimethyl carbonate was prepared by the same procedures as in Example 1 except that the catalyst A was replaced by catalyst C.

At a stage of 2 hours after the start of the reaction, the STY of dimethyl carbonate was 100 g/l·hr and the selectivity thereof was 98%. Also, at a stage of 8 hours after the start of the reaction, the STY of dimethyl carbonate was 92 g/l·hr and the selectivity thereof was 98%. From these results, the catalyst activity reduction D was 1.3%/hr.

EXAMPLE 9

Dimethyl carbonate was prepared by the same procedures as in Example 1 except that the catalyst A was replaced by catalyst D.

At a stage of 2 hours after the start of the reaction, the STY of dimethyl carbonate was 80 g/l·hr and the selectivity thereof was 98%. Also, at a stage of 8 hours after the start of the reaction, the STY of dimethyl carbonate was 79 g/l·hr and the selectivity thereof was 98%. From these results, the catalyst activity reduction D was 0.21%/hr.

EXAMPLE 10

Dimethyl carbonate was produced by the same procedures as in Example 1 except that the mixed material gas did not contain methyl chloroformate, and had a composition of 8% by volume of methyl nitrite, 8% by volume of carbon monoxide, 3% by volume of nitrogen monoxide, 5% by volume of methyl alcohol and 76% by volume of nitrogen, and the reaction temperature was changed to 125° C.

At a stage of 2 hours after the start of the reaction, the STY of dimethyl carbonate was 650 g/l·hr and the selectivity thereof was 93%. This reaction procedure was further continued. At a stage of 10 hours after the start of the reaction, it was found that the STY of dimethyl carbonate was reduced to 279 g/l·hr and the selectivity thereof decreased to 87%. The activity-reduced catalyst was successively employed and to the mixed material gas, which was free from methyl chloroformate, was added 800 ppm of methyl chloroformate. The reaction was further continued by using the methyl chloroformate-containing mixed material gas. At a stage of 2 hours after the addition of methyl chloroformate, the STY of dimethyl carbonate increased to 645 g/l·hr and the selectivity of dimethyl carbonate increased to 93%. Namely, the catalyst activity-enhancing effect due to the addition of methyl chloroformate was confirmed.

COMPARATIVE EXAMPLE 2

The same procedures as in Example 10 were carried out to produce dimethyl carbonate, except that the addition of methyl chloroformate was omitted. At a stage of 2 hours after the re-start of the reaction, the STY of dimethyl carbonate was 235 g/l·hr and the selectivity thereof was 84%.

EXAMPLE 11

Dimethyl carbonate was produced by the same procedures as in Example 1 except that the mixed material gas did not contain methyl chloroformate, and had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 625 g/l·hr and the selectivity thereof was 93%. This reaction procedure was further continued. At a stage of 10 hours after the start of the reaction, it was found that the STY of dimethyl carbonate was reduced to 290 g/l·hr and the selectivity thereof decreased to 88%. To the mixed material gas, which was free from methyl chloroformate, was added 200 ppm of methyl chloroformate. The reaction was further continued by using the methyl chloroformate-containing mixed material gas. At a stage of 2 hours after the addition of methyl chloroformate, the STY of dimethyl carbonate increased to 620 g/l·hr and the selectivity of dimethyl carbonate increased to 93%. Namely, the catalyst activity-enhancing effect due to the addition of methyl chloroformate was confirmed.

EXAMPLE 12

Dimethyl carbonate was produced by the same procedures as in Example 1 except that the mixed material gas did not contain methyl chloroformate, had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 625 g/l·hr and the selectivity thereof was 93%. This reaction procedure was further continued. At a stage of 20 hours after the start of the reaction, it was found that the STY of dimethyl carbonate was reduced to 138 g/l·hr and the selectivity thereof decreased to 76%. To the mixed material gas, which was free from methyl chloroformate, was added 200 ppm of methyl chloroformate. The reaction was further continued by using the methyl chloroformate-containing mixed material gas. At a stage of 2 hours after the addition of methyl chloroformate, the STY of dimethyl carbonate increased to 573 g/l·hr and the selectivity of dimethyl carbonate increased to 92%. Also, at a stage of 4 hours after the addition of methyl chloroformate, the STY of dimethyl carbonate was 693 g/l·hr, and the selectivity thereof was 94%. Further, at a stage of 6 hours after the methyl chloroformate addition, the STY of dimethyl carbonate was 725 g/l·hr and the selectivity thereof was 95%, and at a stage of 8 hours after the methyl chloroformate addition, the STY of dimethyl carbonate was 714 g/l·hr and the selectivity thereof was 95%. Namely, the catalyst activity-enhancing effect due to the addition of methyl chloroformate was confirmed.

EXAMPLE 13

Dimethyl carbonate was produced by the same procedures as in Example 1 except that the mixed material gas did not contain methyl chloroformate, had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 620 g/l·hr and the selectivity thereof was 92%. This reaction procedure was further continued. At a stage of 40 hours after the start of the reaction, it was found that the STY of dimethyl carbonate was reduced to 90 g/l·hr and the selectivity thereof decreased to 68%. To the mixed material gas, which was free from methyl chloroformate, was added 200 ppm of methyl chloroformate. The reaction was further continued by using the methyl chloroformate-containing mixed material gas. At a stage of 2 hours after the addition of methyl chloroformate, the STY of dimethyl carbonate increased to 490 g/l·hr and the selectivity of dimethyl carbonate increased to 92%. Also, at a stage of 4 hours after the addition of methyl chloroformate, the STY of dimethyl carbonate increased to 630 g/l·hr and the selectivity thereof was 93%. Namely, the catalyst activity-enhancing effect due to the addition of methyl chloroformate was confirmed.

EXAMPLE 14

Dimethyl carbonate was produced by the same procedures as in Example 1 except that the mixed material gas did not contain methyl chloroformate, had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 620 g/l·hr and the selectivity thereof was 92%. This reaction procedure was further continued. At a stage of 40 hours after the start of the reaction, it was found that the STY of dimethyl carbonate was reduced to 90 g/l·hr and the selectivity thereof decreased to 68%.

The feed of the material gas to the activity-reduced catalyst was stopped to stop the reaction, and thereafter the temperature of the catalyst layer in the reaction tube was raised up to 180° C. while flowing a nitrogen gas through the reaction tube. Then, the feed of the nitrogen gas was stopped, and a hydrogen gas was flowed through the reaction tube at a feed rate of 80 ml/min for 2 hours while maintaining the catalyst temperature at 180° C., to treat the catalyst with hydrogen. After the hydrogen treatment was completed, the flow of the hydrogen gas was stopped, and the temperature of the catalyst layer was lowered to 125° C. while flowing a nitrogen gas therethrough.

In the condition in which the catalyst layer temperature is maintained at 125° C., the mixed material gas, which was free from methyl chloroformate, was added with 200 ppm of methyl chloroformate. The reaction was re-started by using the resultant mixed material gas. At a stage of 2 hours after the re-start of the reaction, the STY of dimethyl carbonate increased to 640 g/l·hr and the selectivity of dimethyl carbonate increased to 94%. Namely, the catalyst activity-enhancing effect due to the addition of methyl chloroformate was confirmed.

EXAMPLE 15

Dimethyl carbonate was produced by the same procedures as in Example 1 except that the mixed material gas did not contain methyl chloroformate, had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 620 g/l·hr and the selectivity thereof was 92%. This reaction procedure was further continued. At a stage of 300 hours after the start of the reaction, it was found that the STY of dimethyl carbonate was reduced to 8 g/l·hr and the selectivity thereof decreased to 18%.

The feed of the material gas to the activity-reduced catalyst was stopped to stop the reaction, and thereafter the temperature of the catalyst layer in the reaction tube was raised up to 180° C. while flowing a nitrogen gas through the reaction tube. Then, the feed of the nitrogen gas was stopped, and a hydrogen gas was flowed through the reaction tube at a feed rate of 80 ml/min for 2 hours while maintaining the catalyst temperature at 180° C., to treat the catalyst with hydrogen. After the hydrogen treatment was completed, the flow of the hydrogen gas was stopped, and the temperature of the catalyst layer was lowered to 125° C. while flowing a nitrogen gas therethrough.

In the condition in which the catalyst layer temperature is maintained at 125° C., to the mixed material gas, which was free from methyl chloroformate, was added 200 ppm of methyl chloroformate. The reaction was restarted by using the resultant mixed material gas. At a stage of 2 hours after the re-start of the reaction, the STY of dimethyl carbonate increased to 350 g/l·hr and the selectivity of dimethyl carbonate increased to 92%. Namely, the catalyst activity-enhancing effect due to the addition of methyl chloroformate was confirmed.

COMPARATIVE EXAMPLE 3

The same procedures as in Example 15 were carried out to produce dimethyl carbonate, except that the addition of methyl chloroformate was omitted. At a stage of 2 hours after the re-start of the reaction, the STY of dimethyl carbonate was 10 g/l·hr and the selectivity thereof was 10%. Those results were unsatisfactory.

EXAMPLE 16

Dimethyl carbonate was produced by the same procedures as in Example 1 except that the mixed material gas did not contain methyl chloroformate, had a composition of 8% by volume of methyl nitrite, 8% by volume of carbon monoxide, 3% by volume of nitrogen monoxide, 5% by volume of methyl alcohol and 76% by volume of nitrogen and the reaction temperature was changed to 125° C.

At a stage of 2 hours after the start of the reaction, the STY of dimethyl carbonate was 620 g/l·hr and the selectivity thereof was 92%. This reaction procedure was further continued. At a stage of 300 hours after the start of the reaction, it was found that the STY of dimethyl carbonate was reduced to 8 g/l·hr and the selectivity thereof decreased to 18%.

The feed of the material gas to the activity-reduced catalyst was stopped to reduce the reaction rate, and thereafter the temperature of the catalyst layer in the reaction tube was raised up to 200° C. while flowing a nitrogen gas through the reaction tube. Then, the feed of the nitrogen gas was stopped, and a hydrogen gas flows through the reaction tube at a feed rate of 80 ml/min for 8 hours while maintaining the catalyst temperature at 200° C., to treat the catalyst with hydrogen. After the hydrogen treatment was completed, the flow of the hydrogen gas was stopped, and the temperature of the catalyst layer was lowered to 125° C. while flowing a nitrogen gas therethrough.

In the condition in which the catalyst layer temperature is maintained at 125° C., to the mixed material gas, which was free from methyl chloroformate, was added 200 ppm of methyl chloroformate. The reaction was re-started by using the resultant mixed material gas. At a stage of 2 hours after the re-start of the reaction, the STY of dimethyl carbonate increased to 570 g/l·hr and the selectivity of dimethyl carbonate increased to 93%.

The results of the examples and comparative examples are shown in Tables 1 and 2.

TABLE 1

| Example No. | Concentration of methyl chloroformate in mixed material gas (ppm) | Space velocity (GHSV) of mixed material gas ($hr^{-1}$) | 2 hours after the start of reaction STY $Y_0$ (g/l · hr) | Selectivity (%) | 8 hours after the start of reaction STY $T_8$ (g/l · hr) | Selectivity (%) | Catalyst activity reduction (%/hr) |
|---|---|---|---|---|---|---|---|
| Example 1 | 500 | 30000 | 437 | 92 | 464 | 93 | −1.0 |
| Comparative Example 1 | 0 | 30000 | 438 | 92 | 223 | 83 | 8.2 |
| Example 2 | 90 | 30000 | 444 | 94 | 432 | 93 | 0.5 |
| 3 | 60 | 30000 | 314 | 94 | 292 | 92 | 1.2 |
| 4 | 50 | 30000 | 315 | 94 | 270 | 92 | 2.4 |
| 5 | 500 | 30000 | 483 | 92 | 598 | 92 | −4.0 |
| 6 | 500 | 10000 | 402 | 95 | 411 | 94 | −0.4 |
| 7 | 500 | 30000 | 520 | 91 | 502 | 90 | 0.6 |
| 8 | 500 | 30000 | 100 | 98 | 92 | 98 | 1.3 |
| 9 | 500 | 30000 | 80 | 98 | 79 | 98 | 0.2 |

TABLE 2

| Example No. | STY, $Y_0$ at 2 hours after the start of reaction (g/l · hr) | STY, $Y_t$ at t hours after start of reaction (g/l · hr) | Hydrogen treatment conditions for catalyst Temperature-time | Concentration of methyl chloroformate in mixed material gas after the re-start of reaction (ppm) | 2 hours after the re-start of reaction STY, $Y_2$ (g/l · hr) | Selectivity (%) |
|---|---|---|---|---|---|---|
| Example 10 | 650 | $Y_{10}$: 279 | — | 800 | 645 | 93 |
| Comparative Example 2 | 650 | $Y_{10}$: 279 | — | — | 235 | 84 |
| Example 11 | 625 | $Y_{10}$: 290 | — | 200 | 620 | 93 |
| 12 | 625 | $Y_{20}$: 138 | — | 200 | 573 | 92 |
| 13 | 620 | $Y_{40}$: 90 | — | 200 | 490 | 92 |
| 14 | 620 | $Y_{40}$: 90 | 180° C. - 2 hr | 200 | 640 | 94 |
| 15 | 620 | $Y_{300}$: 8 | 180° C. - 2 hr | 200 | 350 | 92 |
| Comparative Example 3 | 620 | $Y_{300}$: 8 | 180° C. - 2 hr | — | 10 | 10 |
| Example 16 | 620 | $Y_{300}$: 8 | 200° C. - 8 hr | 200 | 570 | 93 |

INDUSTRIAL APPLICABILITY

In the process of the present invention in which a carbonic acid diester is produced by a catalytic reaction of carbon monoxide with a nitrous acid ester in the presence of a solid catalyst, the catalyst used can be maintained in a high activity condition over a long time period and thus the carbonic acid diester can be stably produced at a high reaction rate and at a high selectivity for a long period of time, by mixing a small amount of a chloroformic acid ester into a material gas containing the carbon monoxide and nitrous acid ester to be reacted with each other.

We claim:

1. A process for producing a carbonic acid diester comprising catalytically reacting carbon monoxide with a nitrous acid ester in the presence of a solid catalyst in which a platinum group metal or a compound thereof is carried on a carrier, to produce a carbonic acid diester, characterized in that a chloroformic acid ester is mixed into a material gas containing the carbon monoxide and the nitrous acid ester, and the mixed material gas is brought into contact with the solid catalyst.

2. The process as claimed in claim 1, wherein the chloroformic acid ester is selected from chloroformic acid esters of lower aliphatic monohydric alcohols having 1 to 4 carbon atoms, chloroformic acid esters of cycloaliphatic alcohols and chloroformic acid esters of aralkyl alcohols.

3. The process as claimed in claim 2, wherein the chloroformic acid ester is selected from methyl chloroformate, ethyl chloroformate, n-propyl chloroformate, isopropyl chloroformate, n-butyl chloroformate, isobutyl chloroformate, sec-butyl chloroformate, cyclohexyl chloroformate and phenylethyl chloroformate.

4. The process as claimed in claim 2, wherein the chloroformic acid ester is a chloroformic acid ester of a lower aliphatic monohydric alcohol having 1 to 4 carbon atoms.

5. The process as claimed in claim 4, wherein the chloroformic acid ester is selected from methyl chloroformate and ethyl chloroformate.

6. The process as claimed in claim 1, wherein the chloroformic acid ester is contained in a content of 0.001 to 1% by volume in the mixed material gas.

7. The process as claimed in claim 6, wherein the chloroformic acid ester is contained in a content of 50 to 1,000 ppm by volume in the mixed material gas.

8. The process as claimed in claim 1, wherein the nitrous acid ester is selected from nitrous acid esters of lower aliphatic monohydric alcohols having 1 to 4 carbon atoms, nitrous acid esters of cycloaliphatic alcohols and nitrous acid esters of aralkyl alcohols.

9. The process as claimed in claim 8, wherein the nitrous acid ester is selected from nitrous acid esters of lower aliphatic monohydric alcohols having 1 to 4 carbon atoms.

10. The process as claimed in claim 1, wherein the platinum group metal or compound thereof is carried in an amount, in terms of the platinum group metal, of 0.1 to 10% by weight, based on the weight of the carrier.

11. The process as claimed in claim 1, wherein the compound of the platinum group metal is selected from the group consisting of halides, nitrates, sulfates and acetates of the metal.

12. The process as claimed in claim 11, wherein the compound of the platinum group metal is selected from palladium chloride, palladium bromide, palladium nitrate and palladium sulfate.

13. The process as claimed in claim 1, wherein the solid catalyst is one in which the platinum group metal or compound thereof and a compound of at least one metal selected from iron, copper, bismuth, cobalt, nickel and tin are carried on the carrier.

14. The process as claimed in claim 13, wherein the compound of at least one metal selected from the group consisting of iron, copper, bismuth, cobalt, nickel and tin is carried in an amount, in terms of the metal, of 0.1 to 50 gram atom equivalent, based on the amount of the platinum group metal.

15. The process as claimed in claim 1, wherein the reaction of the carbon monoxide with the nitrous acid ester is carried out at a temperature of 0° to 200° C. under a pressure of from the ambient atmospheric pressure to 20 kg/cm$^2$.

16. The process as claimed in claim 1, wherein the carbon monoxide contained in the mixed material gas is present in a concentration of 5 to 20% by volume and the nitrous acid ester in the mixed material gas is present in a concentration of 20% by volume or less.

17. The process as claimed in claim 1, wherein the carbon monoxide and the nitrous acid ester contained in the mixed material gas are present in a molar proportion of 0.1 to 10 moles of the carbon monoxide per mole of the nitrous acid ester.

18. The process as claimed in claim 1, wherein the mixed material gas is fed at a space velocity of 500 to 50,000$^{-1}$.

* * * * *